United States Patent [19]
Labroo et al.

[11] Patent Number: 5,280,040
[45] Date of Patent: Jan. 18, 1994

[54] METHODS FOR REDUCING BONE LOSS USING CENTCHROMAN DERIVATIVES

[75] Inventors: Virender M. Labroo, Mill Creek; James R. Piggott, Bothell; Steven D. Bain, Seattle, all of Wash.

[73] Assignee: ZymoGenetics, Inc., Seattle, Wash.

[21] Appl. No.: 29,729

[22] Filed: Mar. 11, 1993

[51] Int. Cl.$^5$ ................... A61K 31/40; A61K 31/35
[52] U.S. Cl. .................... 514/422; 514/456; 514/428
[58] Field of Search ............... 514/457, 456, 410, 411, 514/422

[56] References Cited

U.S. PATENT DOCUMENTS

| | | | |
|---|---|---|---|
| 3,340,276 | 9/1967 | Carney et al. | 260/345.2 |
| 3,822,287 | 7/1974 | Bolger | 260/326.5 |
| 4,210,644 | 7/1980 | Ewing | 424/239 |
| 4,447,622 | 5/1984 | Salman et al. | 548/525 |
| 4,489,056 | 12/1984 | Himmelstein et al. | 424/22 |
| 4,882,347 | 11/1989 | Cozzi et al. | 514/396 |
| 5,015,661 | 5/1991 | Walser | 514/443 |
| 5,063,234 | 11/1991 | Bryant et al. | 514/288 |

OTHER PUBLICATIONS

CA: vol. 88 (15): No. 99512(v) Kamboj et al (1978).
CA: vol. 117 (7): No. 63184(t)–Singh et al (1992).
Kumari et al., *Contracept.* 13: 665–676, 1976.
Ray et al., *J. Med. Chem.* 19: 276–279, 1976.
Johri et al., *Contracept.* 44: 549–557, 1991.
Salman et al., *J. Med. Chem.* 26: 592–595, 1983.
Bain et al., *J. Bone and Min. Res.* 8: 435–442, 1993.
Liu and Howard, *The Anat. Rec.* 229: 240–250, 1991.
Marie and Hott, *Magnesium* 6: 100–108, 1987.
Frost and Jee, *Bone and Min.* 18: 227–236, 1992.
Marshall et al., *J. Bone and Min. Res.* 5: 955–962, 1990.
Lopez et al., *Exp. Clin. Endocrinol.* 88: 31–38, 1986.
Broulik, *Endocrin. Regul.* 25: 217–219, 1991.
Kalu, *Bone and Min.* 15: 175–192, 1991.
Liu, *Bone and Mineral Reserach* 5(Suppl. 2): S249, 1990.

*Primary Examiner*—Frederick E. Waddell
*Assistant Examiner*—T. J. Criares
*Attorney, Agent, or Firm*—Gary E. Parker; Julie A. Holly

[57] ABSTRACT

Methods and pharmaceutical compositions for reducing bone loss are disclosed. 3,4-diarylchromans and their pharmaceutically acceptable salts are formulated into medicaments for the treatment of bone loss due to osteoporosis or other conditions. An exemplary 3,4-diarylchroman is centchroman (3,4-trans-2,2-dimethyl-3-phenyl-4-[p-(beta-pyrrolidinoethoxy)phenyl]-7-methoxychroman). Formulations include tablets and other forms suitable for oral administration and controlled-release subdermal implants.

13 Claims, 1 Drawing Sheet

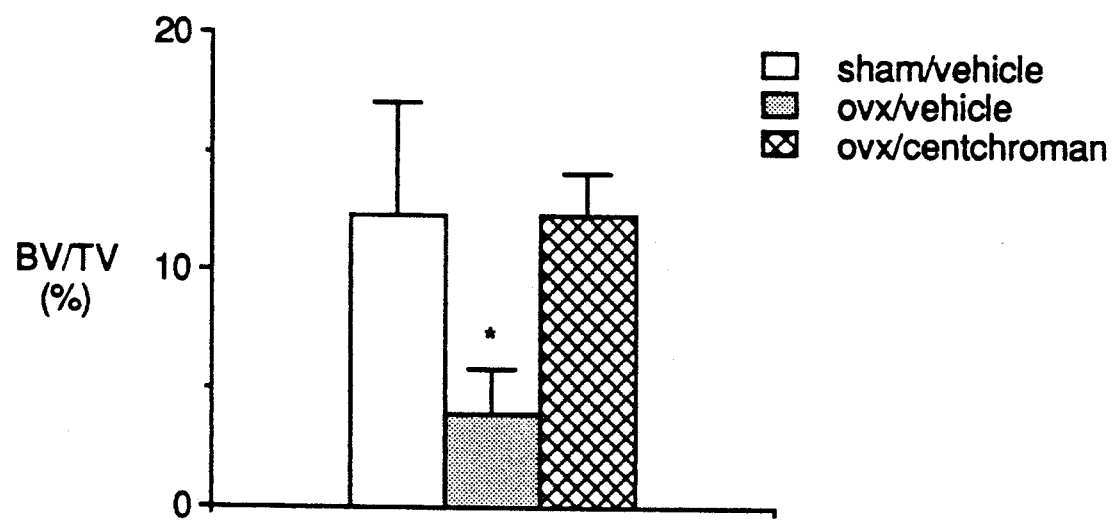
*P<.05 decreased compared to sham animals treated with vehicle and ovx mice treated with centchroman; n = 8 mice/group.

METHODS FOR REDUCING BONE LOSS USING CENTCHROMAN DERIVATIVES

BACKGROUND OF THE INVENTION

Bone remodeling is the dynamic process whereby skeletal mass and architecture are renewed and maintained. This renewal and maintenance is a balance between bone resorption and bone formation, with the osteoclast and the osteoblast considered the two key participants in the remodeling process. The osteoclast initiates the remodeling cycle by resorbing a cavity in the bone which is subsequently refilled when the osteoblast synthesizes and deposits new bone matrix into the excavation. The activities of osteoclast and osteoblast are regulated by complex interactions between systemic hormones and the local production of growth factors and cytokines at active remodeling sites.

Imbalances in bone remodeling are associated with such conditions as osteoporosis, Paget's disease, and hyperparathyroidism. Osteoporosis, characterized by a decrease in the skeletal mass, is one of the most common diseases of postmenopausal women and is often the cause of debilitating and painful fractures of the spine, hip and wrist.

Approximately 25% of all postmenopausal women suffer from osteoporosis, and it is generally accepted that the etiology of the disease involves the reduction of circulating estrogens (Komm et al., Science 241:81-84, 1988). Komm et al. further report that the proportion of caucasian women in the United States who are at risk for a hip fracture is 15%, or 247,000 hip fractures per year in women over the age of 45.

The costs of osteoporosis, both personal and financial, are enormous. In 1984, 145,000 in-patient fracture reductions and 107,000 hip arthroplasties and replacements were performed on American women over 65 years of age. Among patients who lived alone prior to hip fracture, 15% to 20% required long-term care as a result of the fracture and one year after the fracture had still not regained their independence. The total financial cost of osteoporosis treatment, including fractures, in the United States in 1986 was 7-10 billion dollars (Peck et al., Am. J. Med. 84:275-282, 1988).

Bone loss associated with osteoporosis has been arrested by the administration of exogeneous estrogens. To be effective, estrogen therapy must begin within a few years of the onset of menopause, and should continue for 10 to 15 years, according to Thorneycroft (Am. J. Obstet. Gynecol. 160:1306-1310, 1989). While there are several different types of estrogens, 17-β-estradiol is the primary estrogen found naturally occurring in premenopausal women and is often the compound of choice for therapeutic use. At the recommended dose, however, there are significant side effects, the most disturbing being the well-established correlation of estrogen therapy with endometrial and breast cancers. The incidence of carcinoma is both dose-dependent and duration-dependent.

Avoidance of the cancer risk has been achieved by the concomitant use of a progestogen with estrogen. This combination, however, causes menses to return, which many women find unacceptable. A further disadvantage is that the long-term effects of the progestogen have not been fully determined. Thus, a large population of women require alternatives to hormone replacement therapies that can safely prevent the rapid bone loss that accompanies the menopause.

Centchroman is a non-steroidal compound known to have antiestrogenic activity. It is in use in India as an oral contraceptive (see, for example, Salman et al., U.S. Pat. No 4,447,622; Singh et al., Acta Endocrinal (Copenh) 126:444-450, 1992; Grubb, Curr. Opin. Obstet. Gynecol. 3:491-495, 1991; Sankaran et al., Contraception 9:279-289, 1974; Indian Patent No. 129187). Centchroman has also been investigated as an anti-cancer agent for treatment of advanced breast cancer (Misra et al., Int. J. Cancer 43:781-783, 1989), but has not previously been shown to have an effect on bone resorption.

There remains a need in the art for compositions and methods useful in reducing bone loss, in particular bone loss associated with osteoporosis. There is a further need for such compositions that lack the undersirable side effects of estrogens. The present invention provides such compositions and methods and also provides other, related advantages.

BRIEF DESCRIPTION OF THE DRAWING

The Figure illustrates the effects of centchroman on bone loss in ovariectomized mice.

DETAILED DESCRIPTION OF THE INVENTION

The present invention is based in part on the discovery that a representative 3,4-diarylchroman, centchroman (3,4-trans-2,2-dimethyl-3-phenyl-4-[p-(betapyrrolidinoethoxy)phenyl]-7-methoxy-chroman), is an effective inhibitor of bone loss in ovariectomized mice. This animal model mimics the post-menopausal condition and is a generally recognized model of osteoporosis. These data thus indicate that the 3,4-diarylchromans are useful as therapeutic agents for reducing bone loss in mammals, including primates such as humans.

Within the present invention, compounds of formula (I) or their pharmaceutically acceptable salts are used for reducing bone loss in a patient.

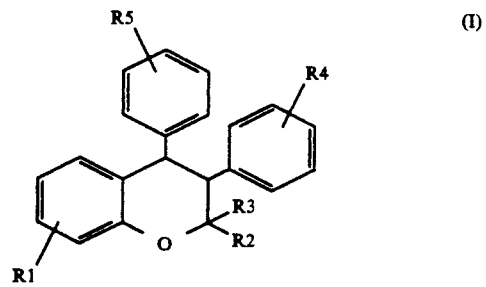

Within formula (I), R1, R4 and R5 are individually hydrogen, halo, trifluoromethyl, lower alkyl, lower alkoxy or tertiary amino lower alkoxy; and R2 and R3 are individually H or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from to 6 carbon atoms, such as methoxy, ethoxy, n-propoxy, isopropoxy, n-butoxy, tert-butoxy, n-amyloxy, sec-amyloxy, n-hexyloxy, 2-ethyl-butoxy, 2,3-dimethylbutoxy and the like. "Halo" includes chloro, fluoro, bromo and iodo. The tertiary amino radical may be a dialkylamine such as a dimethyl, diethyl, dipropyl, dibutyl or polymethyleneimine, e.g. piperidine, pyrrolidine, N-methyl piperazine or morpholine. Preferred compounds include those in which R1 is lower alkoxy; R2 and R3 are lower alkyl, especially methyl; R4 is H; and R5 is tertiary amino lower alkoxy of the polymethyleneimine type. Within particularly preferred embodiments, R1 is in the 7-position and is lower alkoxy, particularly methoxy; each of R2 and R3 is methyl, R4 is H and R5 is in the 4-position and is a tertiary amino lower alkoxy radical such as pyrrolidinoethoxy.

It is preferred to use the compounds of structure (I) in the trans configuration. The l enantiomeric forms are preferred over racemic mixtures.

A particularly preferred compound for use within the present invention is centchroman (II):

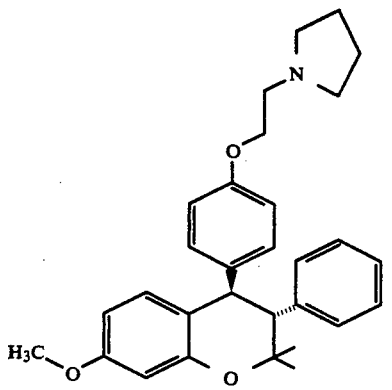
(II)

3,4-diarylchromans are prepared according to known methods, such as those disclosed in U.S. Pat. No. 3,340,276 to Carney et al., U.S. Pat. No. 3,822,287 to Bolger, and Ray et al., *J. Med. Chem.* 19:276-279, 1976, which are incorporated herein by reference. Conversion of the cis isomer to the trans configuration by means of an organometallic base-catalyzed rearrangement is disclosed in U.S. Pat. No. 3,822,287. The optically active d- and l- enantiomers may be prepared as disclosed by Salman et al. in U.S. Pat. No. 4,447,622 (incorporated herein by reference) by forming an optically active acid salt which is subjected to alkaline hydrolysis to produce the desired enantiomer.

Within the present invention, 3,4-diarylchromans may be prepared in the form of pharmaceutically acceptable salts, especially acid-addition salts, including salts of organic acids and mineral acids. Examples of such salts include salts of organic acids such as formic acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulfuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4-diarylchromans and their salts are useful within human and veterinary medicine for the regulation of bone metabolism. These compounds may be used, for example, in the treatment of patients suffering from bone loss due to osteoporosis (including postmenopausal osteoporosis and glucocorticoid-related osteoporosis), Paget's disease, hyperparathyroidism, hypercalcemia of malignancy and other conditions characterized by excessive rates of bone resorption and/or decreased rates of bone formation.

For use within the present invention, 3,4-diarylchromans and their pharmaceutically acceptable salts are formulated with a pharmaceutically acceptable carrier to provide a medicament for parenteral, oral, nasal, rectal, subdermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release subdermal implants, tablets, etc. One skilled in this art may formulate the compounds in an appropriate manner, and in accordance with accepted practices, such as those disclosed in *Remington's Pharmaceutical Sciences*, Gennaro, ed., Mack Publishing Co., Easton, Pa., 1990 (which is incorporated herein by reference in its entirety.)

Oral adiministration is preferred. Thus, the active compound is prepared in a form suitable for oral administration, such as a tablet or capsule. Typically, a pharmaceutically acceptable salt of the compound is combined with a carrier and molded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, coloring, etc.

Pharmaceutical compositions are administered at daily to weekly intervals. An "effective amount" of such a pharmaceutical composition is the amount that provides a clinically significant inhibition of bone loss. Such amounts will depend, in part, on the particular condition to be treated, age, weight, and general health of the patient, and other factors evident to those skilled in the art. In general, inhibition of bone loss is manifested as a statistically significant difference in cancellous bone volume between treatment and control groups. This can be seen as, for example, a 5-10% or more difference in spinal bone mass or bone mineral content over two years. Data from accepted animal models, such as the ovariectomized mouse model of osteoporosis, are generally predictive of doses in humans to within one order of magnitude. For example, therapeutic doses for the treatment of osteoporosis will generally range from 0.01-50 mg/kg/day, preferably 0.05-10 mg/kg/day, most preferably 0.1-5.0 mg/kg/day. The use of cis-isomers or racemic mixtures may necessitate doses in the higher end of the stated range.

The pharmaceutical compositions may be administered in unit dosage form on a daily to weekly basis. In the alternative, they may provided as controlled release formulations suitable for subdermal implantation. Implants are formulated to provide release of active compound over the desired period of time, which can be up to several years. Controlled-release formulations are disclosed by, for example, Sanders et al., *J. Pharm. Sci.* 73: 1294-1297, 1984; U.S. Pat. No. 4,489,056; and U.S. Pat. No. 4,210,644, which are incorporated herein by reference.

The following example is offered by way of illustration, not limitation.

EXAMPLE

The ability of centchroman to prevent osteopenia induced by estrogen deficiency was evaluated in the ovariectomized mouse model. Twenty-four female Swiss-webster mice (8 weeks old) received either an ovariectomy or sham surgery prior to the initiation of a 4 week treatment protocol. For the ovariectomy, a flank incision through the skin, muscle and abdominal peritoneum was made on each side, the ovaries were located and dissected free of adherent fat and connective tissue, and excised. In the sham procedure the ovaries were exteriorized and replaced. In all animals the peritoneum and muscle were sutured together and the skin incisions were closed with wound clips.

Centchroman was dissolved in a minimal amount of dimethylsulfoxide and diluted in oil vehicle to a concentration of 50 µg/100 µl. The mice were treated twice per week for 4 weeks with a subcutaneous injection of centchroman or oil vehicle according to the following outline: Sham/oil vehicle (SV); OVX/oil vehicle; OVX/50 µg centchroman two times per week. There were 8 animals in each group.

At the conclusion of the 4-week centchroman treatment, the mice were anesthetized with ether and sacrificed by cervical dislocation. Immediately after sacrifice, the femurs were removed and fixed in 70% ethyl alcohol (EtOH) and dehydrated in a series of increasing alcohol concentrations: 95% EtOH for 24 hours followed by three changes in 100% EtOH of 24 hours each. After the final 100% EtOH the femurs were cleared in two changes of xylene and then processed undecalcified and embedded in methacrylate plastic according to previously described methods (Bain et al., *Stain Technology* 65: 159–163, 1990). Frontal sections of the distal metaphyses of the femur 5 µm thick were cut on a Reichert-Jung 2050 rotary microtome equipped with a tungsten-carbide knife. The 5 µm sections were mounted on glass slides and stained with Goldner's trichrome stain.

Histomorphometric measurements of the distal metaphyses were determined using the Bioquant Bone Morphometry Program (Biometrics, Inc., Nashville, Tenn.) interfaced via a camera lucida with an Olympus BH-2 light/epifluorescent microscope (Scientific Instruments, Inc., Redmond, Wash.). Morphometric measurements of cancellous bone volume (BV/TV) were performed in the tissue space greater than 0.25 mm from the growth platemetaphyseal junction to exclude primary spongiosa.

Data, shown in the Figure, are expressed as the mean ± SD for each group. Comparison of cancellous bone volumes of the distal femur were based on analysis of variance using Statview TM statistical programs. Treatment differences indicated by the ANOVA were compared using Dunnett's multiple comparison procedure. A P value of less than 0.05 was considered significant.

In ovariectomized mice treated with oil vehicle a 50% decrease in the cancellous bone volume of the distal femur compared to sham animals treated with vehicle was observed. In the ovariectomized animals treated with 50 µg of centchroman twice per week this bone loss was completely prevented.

Although the foregoing invention has been described in some detail by way of illustration and example for purposes of clarity of understanding, it will be evident that certain changes and modifications may be practiced within the scope of the appended claims.

We claim:

1. A method for treating osteoporosis comprising administering to a patient a bone loss inhibiting compound of the formula or a pharmaceutically acceptable salt thereof, wherein $R_1$, $R_4$ and $R_5$ are individually hydrogen, hydroxy, halo, trifluoromethyl, lower alkyl, lower alkoxy or tertiary amino lower alkoxy; and $R_2$ and $R_3$ are individually hydrogen or lower alkyl, in an amount sufficient to inhibit bone resorption.

2. A method according to claim 1 wherein said compound is

3. A method according to claim 1 wherein said compound is administered at a dose of 0.1–5.0 mg/kg patient weight/day.

4. A method according to claim 1 wherein $R_1$ is lower alkoxy, $R_2$ and $R_3$ are lower alkyl, $R_4$ is hydrogen and $R_5$ is tertiary amino lower alkoxy.

5. A method according to claim 1 wherein $R_1$ is methoxy.

6. A method according to claim 1 wherein $R_2$ and $R_3$ are methyl.

7. A method according to claim 1 wherein $R_4$ is hydrogen.

8. A method according to claim 1 wherein $R_5$ is

9. A method according to claim 1 wherein said compound is

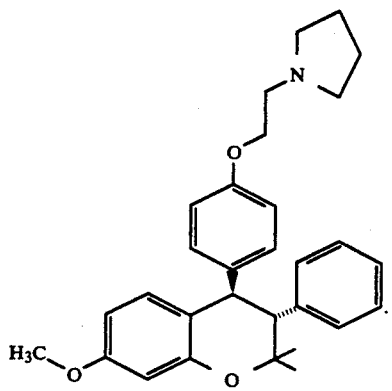

10. A method according to claim 1 wherein said patient is a post-menopausal female.

11. A method according to claim 1 wherein said composition is in a form suitable for oral administration.

12. A method according to claim 1 wherein said composition is administered at daily to weekly intervals.

13. A method according to claim 1 wherein said composition is in the form of a subdermal implant.

* * * * *